US009403777B2

(12) United States Patent
DeGrado et al.

(10) Patent No.: US 9,403,777 B2
(45) Date of Patent: Aug. 2, 2016

(54) INHIBITORS OF THE INFLUENZA A VIRUS M2 PROTON CHANNEL

(71) Applicant: The Trustees Of The University Of Pennsylvania, Philadelphia, PA (US)

(72) Inventors: William F. DeGrado, San Francisco, CA (US); Jun Wang, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 204 days.

(21) Appl. No.: 14/036,813

(22) Filed: Sep. 25, 2013

(65) Prior Publication Data

US 2014/0024635 A1    Jan. 23, 2014

Related U.S. Application Data

(62) Division of application No. 12/848,197, filed on Aug. 1, 2010, now Pat. No. 8,569,284.

(51) Int. Cl.
| | |
|---|---|
| *C07C 255/47* | (2006.01) |
| *C07C 61/13* | (2006.01) |
| *C07C 211/38* | (2006.01) |
| *C07D 223/32* | (2006.01) |
| *C07C 49/447* | (2006.01) |
| *C07C 49/427* | (2006.01) |
| *A61K 31/045* | (2006.01) |
| *A61K 31/122* | (2006.01) |
| *A61K 31/13* | (2006.01) |
| *A61K 31/19* | (2006.01) |
| *A61K 31/277* | (2006.01) |
| *A61K 31/55* | (2006.01) |
| *C07C 35/23* | (2006.01) |
| *C07C 49/323* | (2006.01) |
| *C07C 49/623* | (2006.01) |
| *C07C 211/19* | (2006.01) |

(52) U.S. Cl.
CPC ............ *C07D 223/32* (2013.01); *A61K 31/045* (2013.01); *A61K 31/122* (2013.01); *A61K 31/13* (2013.01); *A61K 31/19* (2013.01); *A61K 31/277* (2013.01); *A61K 31/55* (2013.01); *C07C 35/23* (2013.01); *C07C 49/323* (2013.01); *C07C 49/427* (2013.01); *C07C 49/447* (2013.01); *C07C 49/623* (2013.01); *C07C 61/13* (2013.01); *C07C 211/19* (2013.01); *C07C 211/38* (2013.01); *C07C 255/47* (2013.01); *C07C 2102/50* (2013.01)

(58) Field of Classification Search
None
See application file for complete search history.

(56) References Cited

U.S. PATENT DOCUMENTS

| | | | |
|---|---|---|---|
| 3,214,470 A | 10/1965 | Grogan | |
| 4,005,224 A | 1/1977 | Tankersley, Jr. | |
| 5,849,802 A | 12/1998 | Pfrengle | |
| 2011/0294785 A1* | 12/2011 | DeGrado et al. | ......... 514/212.02 |

OTHER PUBLICATIONS

Balannik Biochemistry vol. 48(5): 11872-11882 (2009).
Bright et al., "Adamantane Resistance Among Influenza A Viruses Isolated Early During the 2005-2006 Influenza Season in the United States", J. Am. Med. Assoc., Feb. 22, 2006, 295(8), 891-894.
Deyde et al., "Surveillance of Resistance to Adamantanes Among Influenza A(H3N2) and A(H1N1) Viruses Isolated Worldwide", J. Infect. Dis., Jul. 15, 2007, 196(2), 249-257.
Grambas et al., "Influence of Amantadine Resistance Mutations on the pH Regulatory Function of the M2 Protein of Influenza A Viruses", Virology, Dec. 1992, 191(2), 541-549.
Hayden, "Antiviral Resistance in Influenza Viruses—Implications for Management and Pandemic Response", N. Eng. J. Med, Feb. 23, 2006, 354(8), 785-788.
Kurtz et al., "Growth Impairment Resulting From Expression of Influenza Virus M2 Protein in *Saccharomyces cerevisiae*: Identification of a Novel Inhibitor of Influenza Virus", Antimicrob Agents Chemother., Oct. 1995, 39(10), 2204-2209.
Tu et al., "Characterization of Inhibition of M2 Ion Channel Activity by BL-1743, an Inhibitor of Influenza A virus", J. Virol., Jul. 1996, 70(7), 4246-4252.

* cited by examiner

*Primary Examiner* — Kamal Saeed
(74) *Attorney, Agent, or Firm* — Baker & Hostetler LLP

(57) ABSTRACT

Provided are compounds that are capable of modulating the activity of the influenza A virus via interaction with the M2 transmembrane protein. Also provided are methods for treating an influenza A-affected disease state or infection comprising administering a composition comprising one or more compounds that have been identified as being capable of interaction with the M2 protein.

10 Claims, 1 Drawing Sheet

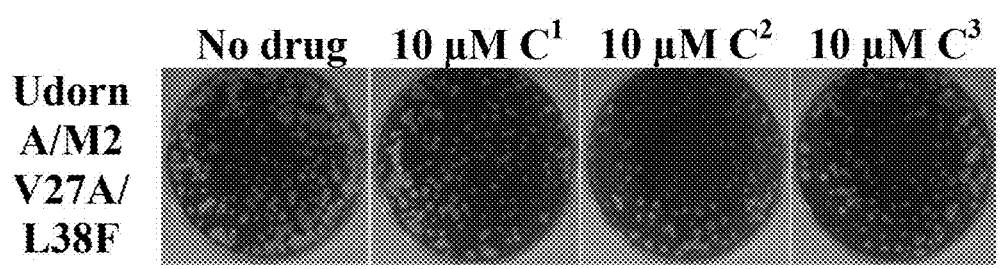
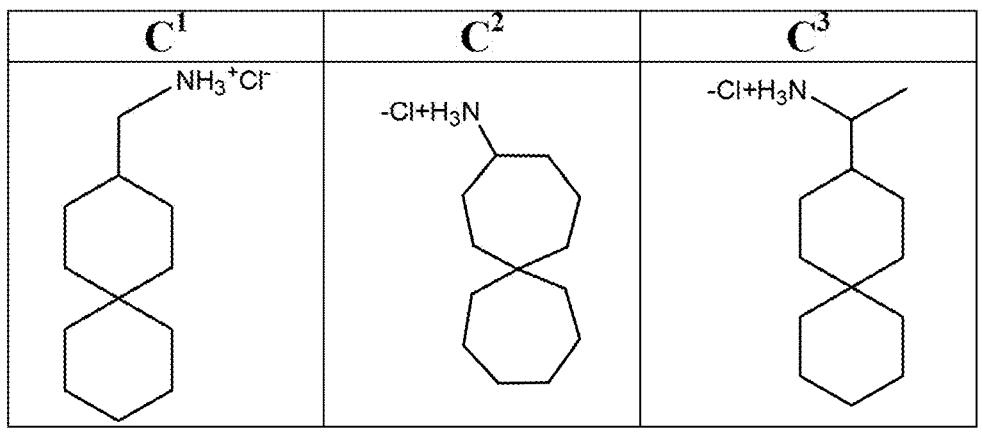

INHIBITORS OF THE INFLUENZA A VIRUS M2 PROTON CHANNEL

CROSS-REFERENCE TO RELATED APPLICATIONS

This application is a divisional of U.S. Ser. No. 12/848,197, filed Aug. 1, 2010 (now allowed), the entire contents of which are hereby incorporated herein by reference.

TECHNICAL FIELD

The present invention pertains to, among other things, compounds and methods for modulating the activity of the influenza virus.

BACKGROUND

The M2 protein is found in the viral envelope of influenza A virus and functions as a highly selective, pH-regulated proton channel important for the life cycle of the virus. Unlike neuraminidase inhibitors, rimantadine and amantadine are anti-viral agents capable of blocking the tetrameric M2 channel. In 2006, the CDC issued an alert instructing clinicians to avoid using M2 ion-channel inhibitors during influenza season due to the extraordinarily high frequency of amantadine resistance in influenza A isolates associated with a single point mutation in the M2 protein, S31N (Hayden F. G., *Antiviral Resistance in Influenza Viruses—Implications for Management and Pandemic Response, N Enj J Med,* 2006, 354;8). The drug-binding site is lined by residues that are mutated in amantadine-resistant viruses. Grambas, S., Bennett, M. S. & Hay, A. J. *Influence of amantadine resistance mutations on the pH regulatory function of the M2 protein of influenza A viruses. Virology* 191, 541-549 (1992); Bright, R. A., Shay, D. K, Shu, B., Cox, N. J. & Klimov, A. I. *Adamantane resistance among influenza A viruses isolated early during the* 2005-2006 *influenza season in the United States. J. Am. Med. Assoc.* 295, 891-894 (2006). Recently, it has been reported that resistance to rimantadine and amantadine in humans, birds and pigs has reached more than 90%, casting into doubt the continued ability of these drugs alone to satisfy the need for treatment of influenza (Deyde, V. M. et al. *Surveillance of resistance to adamantanes among influenza A*(H3N2) *and A*(H1N1) *viruses isolated worldwide. J. Infect. Dis.* 196, 249-257 (2007)).

Previous studies have suggested that BL-1743 (3-(4,5-Dihydro-1H-imidazol-2-yl)-3-aza-spiro[5.5]undecane) interacts differently with the M2 proton channel as compared with amantadine, but have found that the majority of isolated influenza viruses that are amantadine-resistant are also resistant to BL-1743. Tu Q, et al., *Characterization of inhibition of M2 ion channel activity by BL-*1743*, an inhibitor of influenza A virus, J Virol.* 1996 July;70(7):4246-52. For example, Tu Q, et al. found that mutations known to confer amantadine resistance at M2 residues 27, 30, 31, and 34, all within the M2 transmembrane domain, also induce "complete" resistance to BL-1743. Id. The publication by Tu Q, et al. concluded that "the overlapping spectra of amantadine and BL-1743 resistance mutations and the higher apparent $K_i$ . . . do not indicate that BL-1743 should replace the use of amantadine (or rimantadine) for the prophylaxis or treatment of influenza virus infections in humans." Id. See also Kurtz, et al., *Growth impairment resulting from expression of influenza virus M2 protein in Saccharomyces cerevisiae: identification of a novel inhibitor of influenza virus. Antimicrob Agents Chemother.* 1995 October;39(10):2204-9 ("BL-1743 does not produce an additive effect on M2 inhibition, suggesting that these two compounds interact with similar sites in the M2 protein . . . Thus, BL-1743 appears to represent a novel structure with an antiviral profile similar to that of amantadine.").

SUMMARY

In one aspect of the present invention, provided are compounds having the formula (I):

(I)

wherein
X and Y are independently a bond, alkylene, or amine;
$R^1$ and $R^2$ are independently hydrogen, alkyl, hydroxyl, carbonyl, carboxyl, cyano, amino, or —CH($R^5$)($R^6$);
$R^3$ and $R^4$ are independently hydrogen or —CH($R^7$)($R^8$);
$R^5$ and $R^6$ are independently hydrogen, alkyl, hydroxyl, carbonyl, or amino;
$R^7$ and $R^8$ are independently hydrogen, alkyl, alkoxy, hydroxyl, carbonyl, or amino;
dashed lines a and b are optional bonds; and,
n is 0-3,
or a stereoisomer, partial stereoisomer, prodrug, pharmaceutically acceptable salt, hydrate, solvate, acid hydrate, or N-oxide thereof.

In other aspects, methods are provided for treating an influenza A virus-affected disease state or infection comprising the step of administering to a subject in need thereof a composition comprising a compound of formula (I) as described above.

Also disclosed are compositions comprising a compound of formula (I) and a pharmaceutically acceptable carrier, excipient, or diluent.

FIGURES

FIG. 1 depicts the results of a plaque reduction assay of certain compounds according to the present disclosure on A/M2-V27A/L38F mutant influenza virus.

DETAILED DESCRIPTION OF ILLUSTRATIVE EMBODIMENTS

The present invention may be understood more readily by reference to the following detailed description taken in connection with the accompanying examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The disclosures of each patent, patent application, and publication cited or described in this document are hereby incorporated herein by reference, in their entirety.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. Furthermore, when indicating that a certain chemical moiety "may be" X, Y, or Z, it is not intended by such usage to exclude other choices for the moiety; for example, a statement to the effect that $R_1$ "may be alkyl, aryl, or amino" does not exclude other choices for $R_1$, such as halo, aralkyl, and the like.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." In another example, when a listing of possible substituents including "hydrogen, alkyl, and aryl" is provided, the recited listing may be construed as including situations whereby any of "hydrogen, alkyl, and aryl" is negatively excluded; thus, a recitation of "hydrogen, alkyl, and aryl" may be construed as "hydrogen and aryl, but not alkyl", or simply "wherein the substituent is not alkyl".

Protective groups are abbreviated according to the system disclosed in Greene, T. W. and Wuts, P. G. M., *Protective Groups in Organic Synthesis* 2d. Ed., Wiley & Sons, 1991, which is incorporated in its entirety herein. For example, "CBZ" or "Cbz" or "Z" stands for carbobenzyloxy or benzyloxycarbonyl, "Boc" or "BOC" represents t-butoxycarbonyl, "Alloc" denotes allyloxycarbonyl, Bz means benzoyl, and "Fmoc" stands for 9-fluorenylmethoxycarbonyl.

As used herein, the terms "component," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

The abbreviations in the specification correspond to units of measure, techniques, properties, or compounds as follow: "min" means minute(s), "g" means gram(s), "mg" means milligram(s), "µg" means microgram(s), "eq" means equivalent(s), "h" means hour(s), "µL" means microliter(s), "mL" means milliliter(s), "mM" means millimolar, "M" means molar, "mmol" or "mmole" means millimole(s), "cm" means centimeters, "SEM" means standard error of the mean, and "IU" means International Units. "$IC_{50}$ value" or "$IC_{50}$" means dose of the compound which results in 50% alleviation or inhibition of the observed condition or effect.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein). Where appropriate, "alkyl" can mean "alkylene"; for example, if X is —$R_1R_2$, and $R_1$ is said to be "alkyl", then "alkyl" may correctly be interpreted to mean "alkylene".

"Amino" refers to —$NH_2$ and may include one or more substituents that replace hydrogen. "Amino" may be used interchangeably with "amine" and is also intended to include any pharmaceutically acceptable amine salts. For example, amino/amine may refer to —$NH^+(X)(Y)Cl^-$, —NH—, or —$NH^+(X)Cl^-$, wherein X and Y are preferably and independently hydrogen or alkyl, wherein alkyl may include one or more halo substitutions.

As used herein, "aryl", "arene", and "aromatic" each refer to an optionally substituted, saturated or unsaturated, monocyclic, polycyclic, or other homo- or heterocyclic aromatic ring system having from about 3 to about 50 ring members (and all combinations and subcombinations of ranges and specific numbers of carbon atoms therein), with from about 5 to about 10 ring atom members being preferred. Such moieties encompass (include) "heteroaryl" and "heteroarene" as defined infra. Where appropriate, "aryl" can mean "arene"; for example, if X is —$R_1R_2$, and $R_1$ is said to be "aryl", then "aryl" may correctly be interpreted to mean "arene".

As used herein, "alkenyl" refers to an alkyl radical having from about 2 to about 20 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups may be optionally substituted.

As used herein, "aralkyl" refers to alkyl radicals bearing one or more aryl substituents and having from about 4 to about 50 carbon atoms (and all combinations and subcombinations of ranges and specific numbers of carbon atoms therein), wherein aryl and alkyl are as previously defined. In some preferred embodiments, the alkyl moieties of the aralkyl groups have from about 1 to about 4 carbon atoms. In other preferred embodiments, the alkyl moieties have from about 1 to about 3 carbon atoms. Aralkyl groups may be optionally substituted.

"Alkylamino" signifies alkyl-(NH)—, wherein alkyl is as previously described and NH is defined in accordance with the provided definition of amino "Arylamino" represents aryl-(NH)—, wherein aryl is as defined herein and NH is defined in accordance with the provided definition of amino Likewise, "aralkylamino" is used to denote aralkyl-(NH)—, wherein aralkyl is as previously defined and NH is defined in accordance with the provided definition of amino "Alkylamido" refers to alkyl-CH(=O)NH—, wherein alkyl is as previously described. "Alkoxy" as used herein refers to the group R—O— where R is an alkyl group, and alkyl is as previously described. "Aralkoxy" stands for R—O—, wherein R is an aralkyl group as previously defined. "Alkylsulfonyl" means alkyl-$SO_2$—, wherein alkyl is as previously defined.

As used herein, "alkylene" refers to an optionally branched or substituted bivalent alkyl radical having the general formula —$(CH_2)_n$—, where n is 1 to 10. Non-limiting examples include methylene, trimethylene, pentamethylene, and hexamethylene.

As used herein, "heteroaryl" or "heteroarene" refers to an aryl radical wherein in at least one of the rings, one or more of the carbon atom ring members is independently replaced by a heteroatom group selected from the group consisting of S, O, N, and NH, wherein aryl is as previously defined. Heteroaryl/heteroarene groups having a total of from about 3 to about 14 carbon atom ring members and heteroatom ring members are preferred. Likewise, a "heterocyclic ring" is an aryl radical wherein one or more of the carbon atom ring members may be (but are not necessarily) independently replaced by a heteroatom group selected from the group consisting of S, O, N, and NH. Heterocyclic rings having a total from about 3 to 14 ring members and heteroatom ring members are preferred, but not necessarily present; for example, "heterocyclohexyl" may be a six-membered aryl radical with or without a heteroatom group.

"Halo" and "halogen" each refers to a fluoro, chloro, bromo, or iodo moiety, with fluoro, chloro, or bromo being preferred.

"Haloalkyl" signifies halo-alkyl- wherein alkyl and halo, respectively, are as previously described.

The phrase reading "[moiety] is absent" means that the substituents to which the moiety is attached may be directly attached to each other.

Typically, substituted chemical moieties include one or more substituents that replace hydrogen. Exemplary substituents include, for example, halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR''), —N,N-disubstituted amino (—N(R'')R''), oxo (=O), carboxy (—COOH), —O—C(=O)R'', —C(=O)R'', —OR'', —C(=O)OR'', -(alkylene)-C(=O)—OR'', —NHC(=O)R'', aminocarbonyl (—C(=O)NH$_2$), —N-substituted aminocarbonyl (—C(=O)NHR''), —N,N-disubstituted aminocarbonyl (—C(=O)N(R'')R''), thiol, thiolato (—SR''), sulfonic acid (—SO$_3$H), phosphonic acid (—PO$_3$H), —P(=O)(OR'')OR'', —S(=O)R'', —S(=O)$_2$R'', —S(=O)$_2$NH$_2$, —S(=O)$_2$NHR'', —S(=O)$_2$NR''R'', —NHS(=O)$_2$R'', —NR''S(=O)$_2$R'', —CF$_3$, —CF$_2$CF$_3$, —NHC(=O)NHR'', —NHC(=O)NR''R'', —NR''C(=O)NHR'', —NR''C(=O)NR''R'', —NR''C(=O)R'' and the like. In relation to the aforementioned substituents, each moiety R'' can be, independently, any of H, alkyl, cycloalkyl, alkenyl, aryl, aralkyl, heteroaryl, or heterocycloalkyl, for example.

As used herein, the terms "treatment" or "therapy" (as well as different word forms thereof) includes preventative (e.g., prophylactic), curative or palliative treatment.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

"Hydrate" refers to a compound of the present invention which is associated with water in the molecular form, i.e., in which the H—OH bond is not split, and may be represented, for example, by the formula R.H$_2$O, where R is a compound of the invention. A given compound may form more than one hydrate including, for example, monohydrates (R.H$_2$O) or polyhydrates (R.nH$_2$O wherein n is an integer>1) including, for example, dihydrates (R.2H$_2$O), trihydrates (R.3H$_2$O), and the like, or hemihydrates, such as, for example, R.n$_{1/2}$H$_2$O, R.n$_{1/3}$H$_2$O, R.n$_{1/4}$H$_2$O and the like wherein n is an integer.

"Solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n(solvent)) wherein n is an integer>1) including, for example, disolvates (R.2(solvent)), trisolvates (R.3(solvent)), and the like, or hemisolvates, such as, for example, R.n$_{1/2}$(solvent), R.n$_{1/3}$(solvent), R.n$_{1/4}$(solvent) and the like wherein n is an integer. Solvents herein include mixed solvents, for example, methanol/water, and as such, the solvates may incorporate one or more solvents within the solvate.

"Acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

The term "stereoisomers" refers to compounds that have identical chemical constitution, but differ as regards the arrangement of the atoms or groups in space.

"Racemic" means having the capacity for resolution into forms of opposed optical activity.

As used herein, the term "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

"Prodrug" refers to compounds which are themselves inactive or minimally active for the activity desired, but through biotransformation can be converted into biologically active metabolites. For example, a prodrug of the present invention would include, inter alia, any compound which is convertible in vivo by metabolic means to a compound claimed or described in the present disclosure.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

The term "administering" means either directly administering a compound or composition of the present invention, or administering a prodrug, derivative or analog which will form an equivalent amount of the active compound or substance within the body.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

"Subject" or "patient" refers to an embryonic, immature, or adult animal, including the human species, that is treatable with the compositions, and/or methods of the present invention.

Accordingly, in one aspect there are provided compounds having the formula (I):

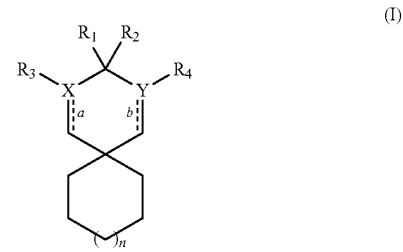

wherein

X and Y are independently a bond, alkylene, or amine;
R$^1$ and R$^2$ are independently hydrogen, alkyl, hydroxyl, carbonyl, carboxyl, cyano, amino, or —CH(R$^5$)(R$^6$);
R$^3$ and R$^4$ are independently hydrogen or —CH(R$^7$)(R$^8$);
R$^5$ and R$^6$ are independently hydrogen, alkyl, hydroxyl, carbonyl, or amino;
R$^7$ and R$^8$ are independently hydrogen, alkyl, alkoxy, hydroxyl, carbonyl, or amino;
dashed lines a and b are optional bonds; and,
n is 0-3,
or a stereoisomer, partial stereoisomer, prodrug, pharmaceutically acceptable salt, hydrate, solvate, acid hydrate, or N-oxide thereof.

With respect to the compounds according to formula (I), certain provisos may apply. These provisos may also optionally apply pursuant to the presently disclosed methods. For example, if n is 1, both X and Y are methylene, and both R$^3$ and R$^4$ are hydrogen, and one of R$^1$ and R$^2$ is hydrogen, then the other of R$^1$ and R$^2$ is not carbonyl.

In certain embodiments X and Y are each independently methylene or ethylene. For example, X is methylene and Y is ethylene, both X and Y are methylene, both X and Y are ethylene, or X is ethylene and Y is methylene. Where X and Y are each independently methylene or ethylene, for example, at least one of R$^1$ and R$^2$ may be hydrogen. In these instances, the other of R$^1$ and R$^2$ may be carbonyl, amino, carboxyl, cyano, or —CH(R$^5$)(R$^6$). In certain examples wherein at least one of R$^1$ and R$^2$ is hydrogen, n is 1 or 2, except that if n is 1, both X and Y are methylene, and both R$^3$ and R$^4$ are hydrogen, then the other of R$^1$ and R$^2$ is not carbonyl. In some instances wherein at least one of R$^1$ and R$^2$ is hydrogen, the other of R$^1$ and R$^2$ is —CH(R$^5$)(R$^6$). For example, one of R$^5$ and R$^6$ may be amino; in such instances, n may be, for example 1 or 2, and X and Y may independently methylene or ethylene, for example, both X and Y are methylene. In other instances wherein at least one of $R^1$ and $R^2$ is hydrogen, and the other of $R^1$ and $R^2$ is —CH($R^5$)($R^6$), one of $R^5$ and $R^6$ may be amino, and the other of $R^5$ and $R^6$ may be hydrogen.

In other instances wherein X and Y are each independently methylene or ethylene, and at least one of $R^1$ and $R^2$ is hydrogen, the other of $R^1$ and $R^2$ is carbonyl; in these examples, if both X and Y are methylene and $R^3$ and $R^4$ are hydrogen, then n is not 1 or 2. In other examples wherein at least one of $R^1$ and $R^2$ is hydrogen, and the other of $R^1$ and $R^2$ is carbonyl, Y may be ethylene.

Where X and Y are each independently methylene or ethylene, and at least one of $R^1$ and $R^2$ is hydrogen, the other of $R^1$ and $R^2$ may be, for example, cyano, amino, carboxyl, or —CH(=O)CH$_3$. In such instances, the other of $R^1$ and $R^2$ may be —NH$_3^+$Cl$^-$.

Exemplary compounds according to the present invention include, among others:

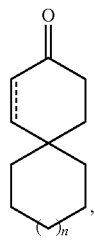

wherein n is 0, 2 or 3;

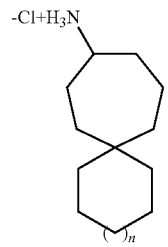 (for example, 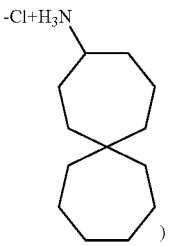);

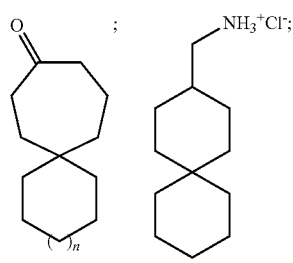 ;  ; 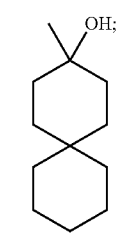 ;

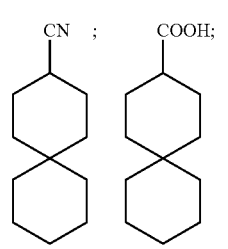 ;  ; 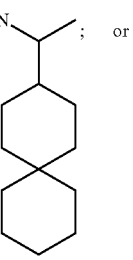 ; 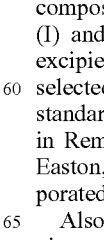 or

-continued

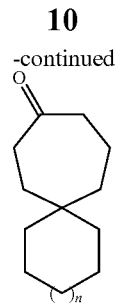

and stereoisomers, partial stereoisomers, prodrugs, pharmaceutically acceptable salts, hydrates, solvates, acid hydrates, and N-oxides thereof The compounds employed in the present invention may exist in prodrug form. As used herein, "prodrug" is intended to include any covalently bonded carriers which release the active parent drug, for example, as according to the formulas or compounds employed in the methods of the present invention in vivo when such prodrug is administered to a subject. Since prodrugs are known to enhance numerous desirable qualities of pharmaceuticals (e.g., solubility, bioavailability, manufacturing, etc.) the compounds of the present invention may, if desired, be delivered in prodrug form. Thus, the present invention contemplates methods of delivering prodrugs. Prodrugs of the compounds employed in the present invention, for example, according to formula (I), may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

In a further aspect, the invention relates to pharmaceutical compositions comprising a compound according to formula (I) and a pharmaceutically acceptable carrier, diluent, or excipient. The applicable carrier, diluent, or excipient may be selected on the basis of the chosen route of administration and standard pharmaceutical practice as described, for example, in Remington's Pharmaceutical Sciences (Mack Pub. Co., Easton, Pa., 1985), the disclosure of which is hereby incorporated by reference in its entirety.

Also provided are methods for treating an influenza A virus-affected disease state or infection comprising the step of administering to a subject in need thereof a composition comprising a compound of formula (I), wherein any of the embodiments of compounds of formula (I) that are disclosed herein may be used in accordance with the present methods.

The influenza A virus-affected disease state or infection may comprise any condition that arises as a direct or indirect result of the presence of influenza A virus. For example, the influenza A virus-affected disease state may comprise influenza (flu), pneumonia, bronchitis, sinus infection, or ear infection, among other conditions. The disease state or infection may arise as a direct or indirect result of the presence of wild-type influenza A virus, or may arise as a direct or indirect result of the presence of a mutant version of the influenza A virus, or may arise as a direct or indirect result of the presence of both a wild-type influenza A virus and a mutant version of the influenza A virus. Thus, in accordance with the present methods, the influenza A virus may be wild-type or may be a mutant virus. The mutant virus may comprise an influenza A virus having the L26F mutation; may comprise an influenza A virus having the V27G mutation, the V27I mutation, the V27T mutation, the V27S mutation, or the V27A mutation; may comprise an influenza virus having the A30T mutation; may comprise an influenza virus having the S31A mutation or the S31N mutation; may an influenza virus having the G34E mutation or the G34A mutation; may comprise an influenza virus having the L38F mutation; may comprise an influenza virus having the W41L mutation or the W41Y mutation; may comprise an influenza virus having the D44N mutation or the D44H mutation; and/or may comprise an influenza virus having the R45K mutation or the R45H mutation.

The compounds of this invention may be administered orally or parenterally, neat or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavors, or printing ink. Of course, any material used in preparing any dosage unit form is preferably pharmaceutically pure and substantially non-toxic in the amounts employed. In addition, the active compound may be incorporated into sustained-release preparations and formulations. Parenteral administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. The therapeutic compositions preferably contain up to about 99% of the active ingredient.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient or ingredients, plus any additional desired ingredient from the previously sterile-filtered solution thereof.

The compounds of the invention may be administered in an effective amount by any of the conventional techniques well-established in the medical field. The compounds employed in the methods of the present invention including, for example, the compounds of formula I or II may be administered by any means that results in the contact of the active agents with the agents' site or sites of action in the body of a patient. The compounds may be administered by any conventional means available.

Preferably the pharmaceutical composition is in unit dosage form, e.g. as tablets, buccal tablets, troches, capsules, elixirs, powders, solutions, suspensions, emulsions, syrups, wafers, granules, suppositories, or the like. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. In addition, dosage forms of the present invention can be in the form of capsules wherein one active ingredient is compressed into a tablet or in the form of a plurality of microtablets, particles, granules or non-perils. These microtablets, particles, granules or non-perils are then placed into a capsule or compressed into a capsule, possibly along with a granulation of the another active ingredient.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The dose may also be provided by controlled release of the compound, by techniques well known to those in the art.

The compounds useful in the methods of the present invention may be prepared in a number of ways well known to those skilled in the art. The compounds can be synthesized, for example, by the methods as described below, or variations thereon as appreciated by the skilled artisan. The reagents used in the preparation of the compounds of this invention can be either commercially obtained or can be prepared by standard procedures described in the literature. All processes disclosed in association with the present invention are contemplated to be practiced on any scale, including milligram, gram, multigram, kilogram, multikilogram or commercial industrial scale.

The present invention is further defined in the following Examples. It should be understood that these examples, while indicating preferred embodiments of the invention, are given by way of illustration only, and should not be construed as limiting the appended claims From the above discussion and these examples, one skilled in the art can ascertain the essential characteristics of this invention, and without departing from the spirit and scope thereof, can make various changes and modifications of the invention to adapt it to various usages and conditions.

EXAMPLES

All chemicals for use in preparing the inventive compounds were purchased from commercial vendors and used without further purification, unless otherwise noted.

Example 1

Synthesis and Inhibition Activity of Exemplary Influenza A M2 Proton Channel Inhibitors All chemicals were purchased from commercial vendors and used without further purification unless otherwise noted. $^1$H and $^{13}$C NMR spectra were recorded on a DMX-360 NMR spectrometer. Chemical shifts are reported in parts per million referenced with respect to residual solvent (CHCl$_3$) 7.26 ppm and (DMSO-d$_6$) 2.50 ppm or from internal standard tetramethylsilane (TMS) 0.00 ppm. The following abbreviations were used in reporting spectra: s) singlet, d) doublet, t) triplet, q) quartet, m) multiplet, dd) doublet of doublets. All reactions were carried out under a N$_2$ atmosphere, unless otherwise stated. HPLC grade solvents were used for all the reactions. Column chromatography was performed using silica gel (230-400 mesh). Low-resolution mass spectra were obtained using an ESI technique on 3200 Q Trap LC/MS/MS system (applied biosystem).

Synthesis of some embodiments was accomplished as illustrated in the following generalized schematic and as described below:

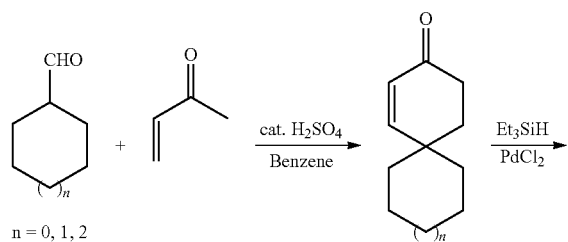
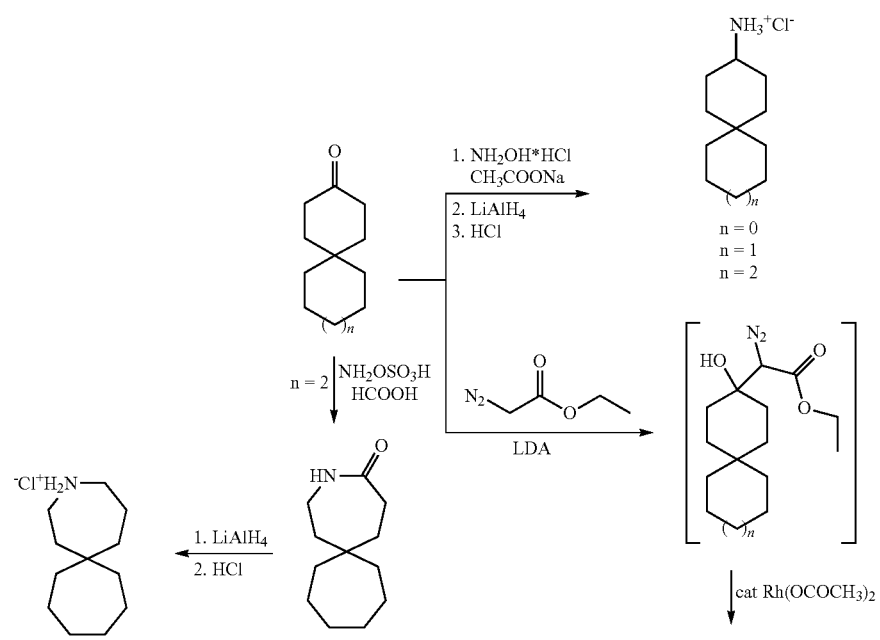
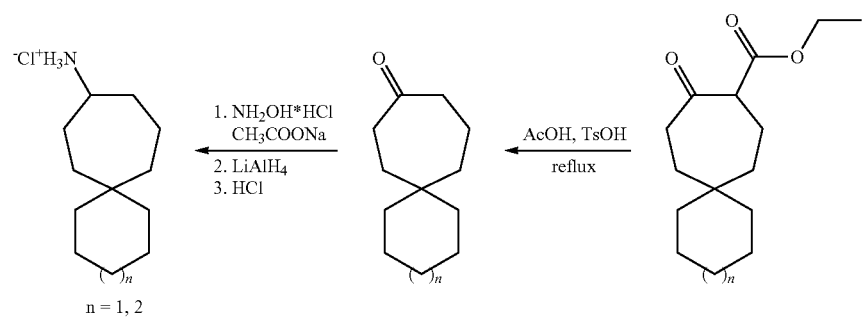

The following schematic represents the process by which some additional inventive compounds were prepared:

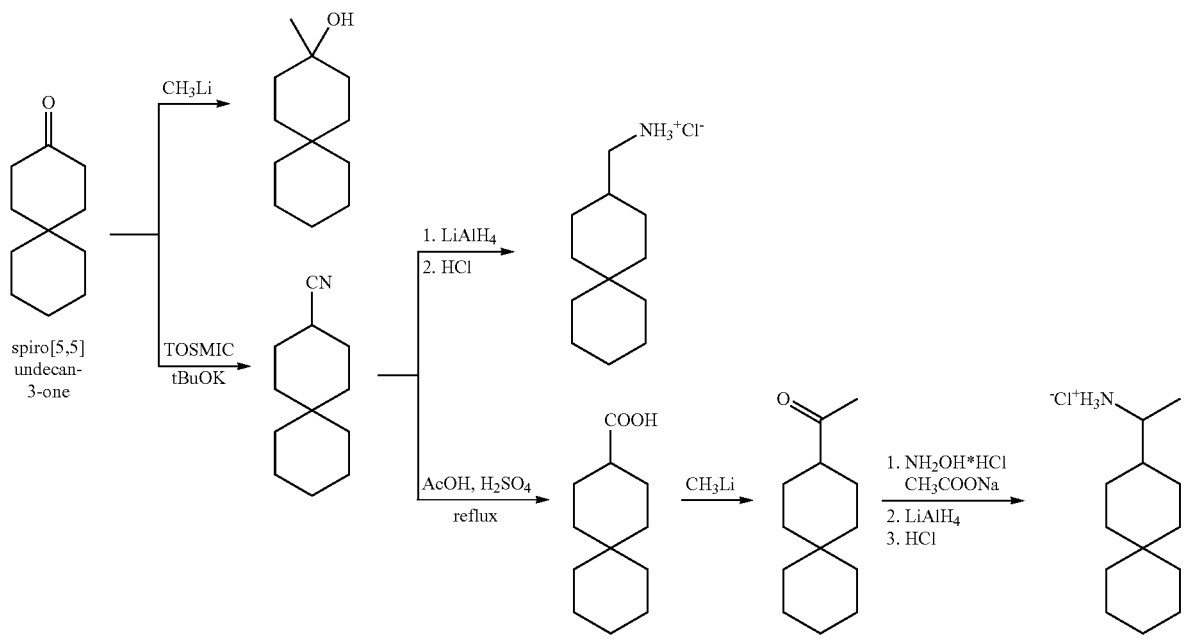

The general procedure for the acid catalyzed robinson annulation reaction is as follows:

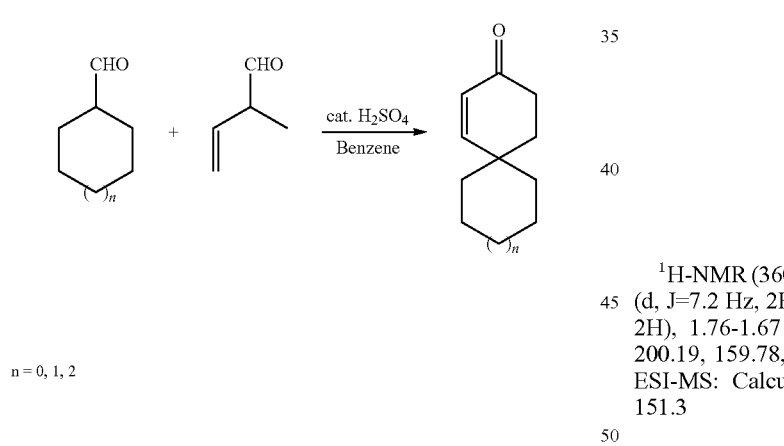

n = 0, 1, 2

Carbaldehyde (10 mmol), but-3-en-2-one (10 mmol) was refluxed in benzene (10 ml) with catalytic amount $H_2SO_4$ (0.05ml) in a round bottom flask equipped with Dean-Stark trap. The mixture was first heated to 45° C. for 1.5 hrs, and then increased to reflux until no more $H_2O$ condensed from the reaction mixture (1.5 hr). Another equivalent of bu-3-2-one (10mmol) was added and refluxed for an additional 1.5 hrs. The mixture was cooled down and 20ml of 1 M $NaHCO_3$ was added and the organic phase was separated. The aqueous phase was extracted with benzene, and the combined organic phase was washed with brine and dried over $MgSO_4$. The solid was filtered, and concentrated in vacuo to give crude dark brown oil which was separated by flash column chromatography (Ethyl acetate/Hexane=15% to 25%) to give Spiro enone as yellow oil.

Spiro[4.5]dec-6-en-8-one (65% Yield)

$^1$H-NMR (360 MHz, $CDCl_3$) δ 6.74 (d, J=7.2 Hz, 2H), 5.84 (d, J=7.2 Hz, 2H), 2.44 (t, J=7.2 Hz, 2H), 1.89 (t, J=7.2 Hz, 2H), 1.76-1.67 (m, 8H); $^{13}$C-NMR (90 MHz, $CDCl_3$) δ 200.19, 159.78, 126.76, 44.32, 38.31, 35.59, 34.15, 24.73; ESI-MS: Calculated for $C_{10}H_{14}O(M+H)^+$ 151.2, Found: 151.3

Spiro[5.6]dodec-1-en-3-one $^1$H-NMR (360 MHz, $CDCl_3$) δ 6.75 (d, J=7.2 Hz, 2H), 5.79 (d, J=7.2 Hz, 2H), 2.39 (t, J=7.2 Hz, 2H), 1.81 (t, J=7.2 Hz, 2H), 1.62-1.49 (m, 12H); $^{13}$C-NMR (90 MHz, CDCl$_3$) δ 199.89, 159.40, 126.02, 38.26, 37.81, 34.18, 33.61, 30.65, 23.10; ESI-MS: Calculated for C$_{12}$H$_{18}$O (M+H)$^+$ 179.3, Found: 179.3

The general procedure for reduction of Spiro enone with PdCl$_2$/Et$_3$SiH is as follows:

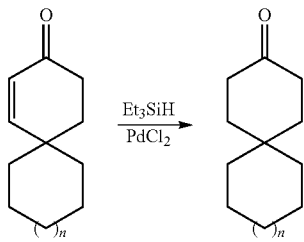

To spiro enone (10 mmol) in absolute EtOH was added PdCl$_2$ (0.2g), Et$_3$SiH (20mmol) was added dropwise to the mixture with stirring. The mixture was refluxed for 4 hrs and PdCl$_2$ was filtered, washed with EtOH. The filtrate was concentrated and purified by flash column chromatography (Ethyl acetate/ Hexane=15% to 25%) to give spiro ketone as yellow oil.

Spiro[4.5]decan-8-one (85% Yield)

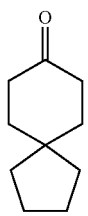 [SMILES: O=C1CCC2(CCCC2)CC1]

$^1$H-NMR (360 MHz, CDCl$_3$) δ 2.34 (t, J=7.2 Hz, 2H), 1.76 (t, J=7.2 Hz, 2H), 1.71-1.67 (m, 4H), 1.59-1.55 (m, 4H); $^{13}$C-NMR (90 MHz, CDCl$_3$) δ 212.97, 42.15, 39.31, 37.95, 37.48, 24.73; ESI-MS: Calculated for C$_{10}$H$_{16}$O (M+H)$^+$ 153.2, Found: 153.2

Spiro[5.6]dodecan-3-one (88% Yield)

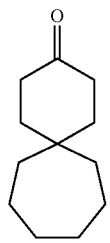

$^1$H-NMR (360 MHz, CDCl$_3$) δ 2.31 (t, J=7.2 Hz, 2H), 1.67 (t, J=7.2 Hz, 2H), 1.57-1.50 (m, 12H); $^{13}$C-NMR (90 MHz, CDCl$_3$) δ 213.32, 38.65, 37.81, 37.71, 35.25, 30.66, 23.17; ESI-MS: Calculated for C$_{12}$H$_{20}$ (M+H)$^+$ 181.3, Found: 181.3

The general procedure for reductive amination of Spiro ketone is as follows:

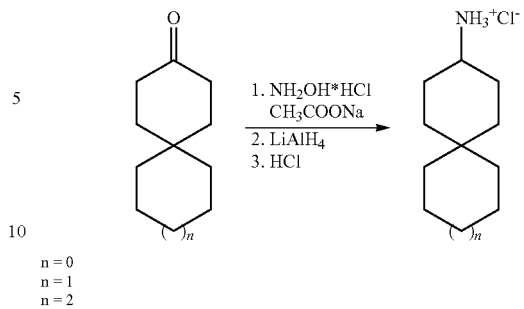

n = 0
n = 1
n = 2

To a solution of spiro ketone (10 mmol) in EtOH (50 ml) was added HONH$_2$*HCl (30 mmol) and NaOAc (40 mmol). The mixture was heated to reflux for 2 hrs. Solvent was removed in vacuo and the residue was extracted with CH$_2$Cl$_2$ and H$_2$O. The aqueous layer was extracted with CH$_2$Cl$_2$ again. The combined CH$_2$Cl$_2$ was dried with MgSO$_4$ and concentrated in vacuo. The resulting oxime was dissolved in anhydrous THF and cooled down to 0° C. LiAlH$_4$ (0.80 g, 20 mmol) was added portionwise to the solution and the mixture was heated to reflux overnight. After cooling down to 0° C., the solution was quenched with H$_2$O (0.8 mL), 15% NaOH (0.8 mL), and H$_2$O (2.4 mL) sequentially. The resulting slurry was filtered. The filtrate was acidified with 4M HCl in 1,4-dioxane and concentrated in vacuo. The final product was purified by flash chromatography to give spirane amine hydrochloride salt as yellow solid.

Spiro[4.5]decan-8-aminium chloride (the Preceding Molecule Wherein n=0) (Yield: 75%)

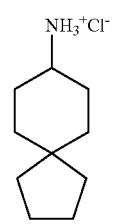

$^1$H-NMR (360 MHz, CDCl$_3$) δ 3.12-3.08 (m, 1H), 1.67-1.45 (m, 16H); $^{13}$C-NMR (90 MHz, CDCl$_3$) δ 52.53, 42.96, 37.54, 36.52, 29.96, 26.63; ESI-MS: Calculated for C$_{10}$H$_{19}$N (M+H)$^+$ 154.3, Found: 154.3.

Spiro[5.5]undecan-3-aminium chloride

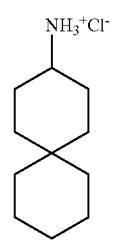

Spiro[5.6]dodecan-3-aminium chloride (Yield: 72%)

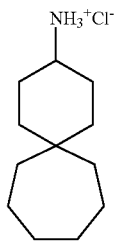

¹H-NMR (360 MHz, CDCl₃) δ 3.12-3.08 (m, 1H), 1.67-1.45 (m, 16H); ¹³C-NMR (90 MHz, CDCl₃) δ 52.70, 45.53, 37.93, 36.51, 36.24, 32.64, 32.32, 28.20, 24.74, 24.55; ESI-MS: Calculated for $C_{12}H_{23}N$ (M+H)⁺ 182.3, Found: 182.3.

The compound 3-azaspiro[6.6]tridecan-3-ium chloride was prepared as follows:

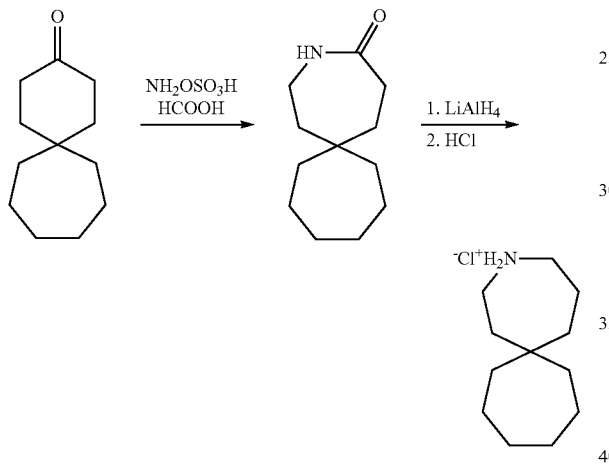

To a solution of hydroxylamine-O-sulfonic acid (1.70 g, 15 mmol) and 95% formic acid (9 ml) under N₂ protection was added dropwise spiro[5.6]dodecan-3-one (1.80 g, 10 mmol) in 3 ml of 95% formic acid. The solution was heated under reflux for 5 hrs and then cooled to ambient temperature. The reaction mixture was diluted with H₂O (15 ml) and neutralized to pH 7 with 6 N NaOH. The aqueous solution was extracted three times with 30 ml CHCl₃. The combined organic layer was dried with MgSO₄ and used for the next step reduction without purification. 3-azaspiro[6.6]tridecan-4-one was dissolved in anhydrous THF and cooled down to 0° C. LiAlH₄ (0.80 g, 20 mmol) was added portionwise to the solution and the mixture was heated to reflux overnight. After cooling down to 0° C., the solution was quenched with H₂O (0.8 mL), 15% NaOH (0.8 mL), and H₂O (2.4 mL) sequentially. The resulting slurry was filtered. The filtrate was acidified with 4M HCl in 1,4-dioxane and concentrated in vacuo. The final product was purified by flash chromatography to give 3-azaspiro[6.6]tridecan-3-ium chloride as yellow solid (1.35 g, 62% Yield). ¹H-NMR (360 MHz, CD₃OD) δ 3.31-3.27 (m, 2H), 3.12-3.10 (m, 2H), 1.73-1.65 (m, 4H), 1.52-1.47 (m, 6H), 1.30-1.27 (m, 8H); ¹³C-NMR (90 MHz, CD₃OD) δ 43.42, 40.75, 39.52, 39.47, 37.51, 36.64, 32.18, 23.76, 21.73; ESI-MS: Calculated for $C_{12}H_{23}N$ (M+H)⁺ 182.3, Found: 182.5.

The general procedure for the reaction used to accomplish ring expansion was as follows:

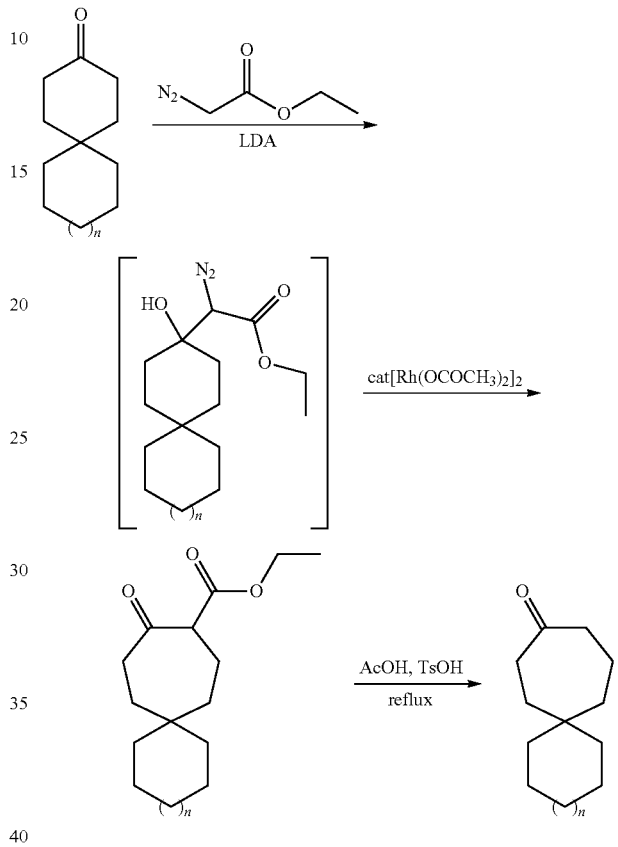

To a solution of spiro ketone (5 mmol) and ethyl diazoacetate (1.15 g, 10 mmol) in anhydrous THF (20 ml) at −78° C. was added LDA (5 ml, 2M in hexane) dropwise under N₂ atmosphere. The reaction was stirred at the same temperature for 2hrs and warmed to ambient temperature. Aqueous NH₄Cl (40 ml, 30% w/w) was added and extracted with diethyl ether. The combined organic layers were washed with water, brine, dried over anhydrous MgSO₄, filtered and concentrated in vacuo to give the diazo-hyroxyl ester intermediate as brown oil. CH₂Cl₂ (30 ml) was added and the flask was flushed with N₂ atmosphere. Rodium(II) acetate dimer (8 mg) was then added and the mixture was stirred at ambient temperature for 1 hr. The catalyst was filtered and the filtrate was concentrated in vacuo to give the crude β-keto ester as yellow oil which was used for the next step hydrolysis without further purification. To a solution of 0 -keto ester, acetic acid (10 ml), water (5 ml) was added para-toluenesulfonic acid (1 mmol, 0.19 g). The solution was heated to reflux for 24 hrs. After cooling to ambient temperature, the reaction mixture was diluted with water (20 ml) and extracted with diethyl ether (30 ml×3). The combined ether was dried over anhydrous MgSO4 and purified by flash column chromatography (20-30% Ethyl acetate/Hexane) to give spiran ketone as yellow oil.

Spiro[5.6]dodecan-9-one (Yield: 72%)

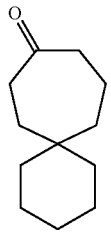 [SMILES: O=C1CCCC2(CCCCC2)CC1]

$^1$H-NMR (360 MHz, CDCl$_3$) δ 2.47 (t, J=7.2 Hz, 2H), 2.42 (t, J=7.2 Hz, 2H), 1.67-1.62 (m, 4H), 1.52-1.30 (m, 12H); $^{13}$C-NMR (90 MHz, CDCl$_3$) δ 211.23, 43.95, 41.72, 38.81, 36.69, 35.39, 33.04, 26.69, 21.82, 19.31; ESI-MS: Calculated for C$_{12}$H$_{20}$O (M+H)$^+$ 181.3, Found: 181.1.

Spiro[6.6]tridecan-3-one (Yield: 75%)

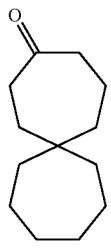 [SMILES: O=C1CCCC2(CCCCCC2)CC1]

$^1$H-NMR (360 MHz, CDCl$_3$) δ 2.46 (t, J=7.2 Hz, 2H), 2.40 (t, J=7.2 Hz, 2H), 1.70-1.63 (m, 2H), 1.59-1.55 (m, 2H), 1.51-1.41 (m, 14H); $^{13}$C-NMR (90 MHz, CDCl$_3$) δ 215.17, 43.96, 41.44, 39.08, 39.03, 38.76, 35.24, 31.11, 22.80, 19.54; ESI-MS: Calculated for C$_{13}$H$_{22}$) (M+H)$^+$ 195.3, Found: 195.4.

The compound spiro[5.6]dodecan-9-aminium chloride was synthesized according to the general reductive amination procedure. (Yield: 70%)

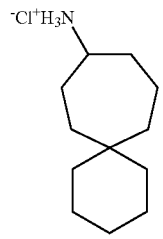

$^1$H-NMR (360 MHz, CD$_3$OD) δ 3.18-3.13 (m, 1H), 1.78-1.61 (m, 6H), 1.47-1.37 (m, 10H), 1.36-1.29 (m, 4H); $^{13}$C-NMR (90 MHz, CD$_3$OD) δ 83.25, 67.76, 67.56, 64.45, 64.25, 56.25, 55.71, 51.08, 51.06, 48.02; ESI-MS: Calculated for C$_{12}$H$_{23}$N (M+H)$^+$ 182.3, Found: 182.4.

The compound spiro[6.6]tridecan-3-aminium chloride was synthesized according to the general reductive amination procedure (Yield: 75%)

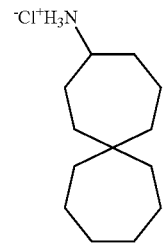

$^1$H-NMR (360 MHz, CD$_3$OD) δ 3.14-3.13 (m, 1H), 1.74-1.48 (m, 12H), 1.48-1.28 (m, 6H), 1.18-1.09 (m, 4H); $^{13}$C-NMR (90 MHz, CD$_3$OD) δ 55.47, 41.03, 41.01, 40.40, 39.88, 36.65, 35.82, 32.51, 28.39, 23.91, 23.87, 20.08; ESI-MS: Calculated for C$_{13}$H$_{25}$N (M+H)$^+$ 196.3, Found: 196.3.

Spiro[5.5]undecane-3-carbonitrile

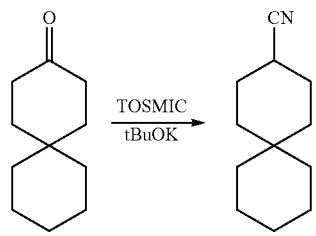 [SMILES: "tBuOK" ; O=C1CCC2(CCCCC2)CC1 ; N#CC1CCC2(CCCCC2)CC1]

To a solution of spiro[5.5]undecan-3-one (1.66 g, 10 mmol) and tosylmethylisocyanide (2.54 g, 13 mmol) in DME (50 ml) and abs. EtOH (1 ml) was added KO$^t$Bu (2.69 g, 24 mmol) portionwise during 0.5 hr at −10° C. After addition, the reaction mixture was stirred at 0° C. for 1 hr then 2 hr at ambient temperature. Solvent was removed in vacuo and the resulting residue was extracted with diethyl ether (50 ml×3) and the combined organic layer was washed with water (50 ml ×3). The organic layer was dried with anhydrous MgSO$_4$, concentrated under reduced pressure and purified by flash column chromatography (50% -100% CH$_2$Cl$_2$/Hexane) to give the nitrile as colorless solid (1.28 g, 72% Yield). $^1$H-NMR (360 MHz, CDCl$_3$) δ 2.58-2.53 (m, 1H), 1.83-1.70 (m, 4H), 1.63-1.58 (m, 2H), 1.40-1.26 (m, 8H), 1.28-1.20 (m, 4H); $^{13}$C-NMR (90 MHz, CDCl$_3$) δ 122.79, 34.41, 31.88, 28.37, 26.88, 24.73, 21.64, 21.55; ESI-MS: Calculated for C$_{12}$H$_{19}$N (M+H)$^+$ 178.3, Found: 178.2.

Spiro[5.5]undecan-3-ylmethanaminium chloride

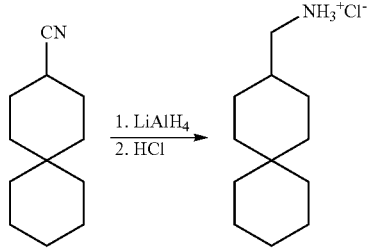

Spiro[5.5]undecane-3-carbonitrile (1.77 g, 10 mmol) in anhydrous THF was cooled down to 0° C. LiAlH$_4$ (0.80 g, 20 mmol) was added portionwise to the solution and the mixture was heated to reflux overnight. After cooling down to 0° C., the solution was quenched with H$_2$O (0.8 mL), 15% NaOH (0.8 mL), and H$_2$O (2.4 mL) sequentially. The resulting slurry was filtered. The filtrate was acidified with 4M HCl in 1,4-dioxane and concentrated in vacuo. The final product was purified by flash chromatography to give spiro[5.5]undecan-3-ylmethanaminium chloride as yellow solid (1.70 g, 78% Yield). $^1$H-NMR (360 MHz, CD$_3$OD) δ 3.10-3.06 (m, 2H), 2.58-2.54 (m, 1H), 1.49-1.45 (m, 2H), 1.34-1.32 (m, 2H), 1.68-1.64 (m, 8H), 0.98-0.81 (m, 6H); $^{13}$C-NMR (90 MHz, CD$_3$OD) δ 46.54, 42.61, 37.87, 36.97, 33.25, 33.20, 28.07, 26.32, 22.83, 22.69; ESI-MS: Calculated for C$_{12}$H$_{23}$N (M+H)$^+$ 182.3, Found: 182.3.

Spiro[5.5]undecane-3-carboxylic acid

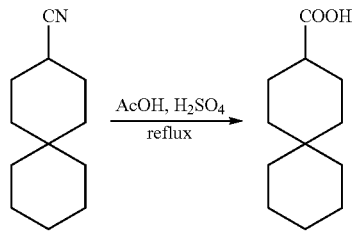 [SMILES: N#CC1CCC2(CCCCC2)CC1 ; "reflux" ; O=C(O)C1CCC2(CCCCC2)CC1]

Spiro[5.5]undecane-3-carbonitrile (1.77 g, 10 mmol) was dissolved in AcOH (20 ml), H$_2$SO$_4$ (5m1) and H$_2$O (10 ml) was added and the mixture was heated to reflux overnight. The solution was cooled down to ambient temperature and diluted with H$_2$O (100 ml). The aqueous layer was extracted with diethyl ether (100 ml×3), the combined organic layer was dried over MgSO$_4$ and concentrated in vacuo. The product was purified by flash column chromatography (10%-20% CH$_3$OH/CH$_2$Cl$_2$) to give colorless solid (1.53 g, 78% Yield). $^1$H-NMR (360 MHz, CDCl$_3$) δ 2.32-2.25 (m, 1H), 1.78-1.58 (m, 6H), 1.52-1.35 (m, 8H), 1.24-1.21 (m, 2H), 1.12-1.04 (m, 2H); $^{13}$C-NMR (90 MHz, CDCl$_3$) δ 183.13, 43.55, 40.96, 35.78, 32.75, 32.05, 27.10, 23.97, 21.86, 21.71; ESI-MS: Calculated for C$_{12}$H$_{20}$O$_2$ (M−H)$^+$ 195.3, Found: 195.3

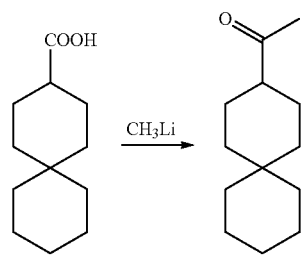

Spiro[5.5]undecane-3-carboxylic acid (1.96 g, 10 mmol) in anhydrous diethyl ether (50 ml) was cooled down to 0° C., CH$_3$Li (22 mmol) was added dropwise in 30 mins The resulting mixture was stirred at the same temperature for two more hours and warmed to ambient temperature overnight. Saturated NH$_4$Cl aqueous solution was added and was extracted with diethyl ether (50 ml×3). The organic layers were combined and dried over anhydrous MgSO$_4$. The product was purified by flash column chromatography (20%-30% Ethyl acetate/Hexane) as yellow oil (1.40 g, 72% Yield)$^1$H-NMR (360 MHz, CDCl$_3$) δ 2.30-2.22 (m, 1H), 2.11 (s, 3H), 1.71- 1.63 (m, 4H), 1.55-1.47 (m, 2H), 1.47-1.36 (m, 8H), 1.23-1.20 (m, 2H), 1.87-1.01 (m, 2H); $^{13}$C-NMR (90 MHz, CDCl$_3$) δ 212.44, 52.07, 41.32, 36.05, 32.39, 32.15, 28.10, 27.07, 23.60, 21.84, 21.67; ESI-MS: Calculated for C$_{13}$H$_{22}$O (M+H)$^+$ 195.3, Found: 195.3

1-(spiro[5.5]undecan-3-yl)ethanaminium chloride

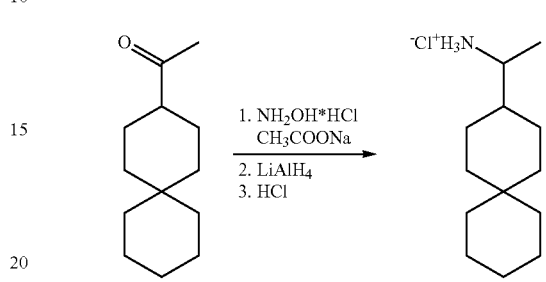

1-(spiro[5.5]undecan-3-yl)ethanaminium chloride was synthesized according to the procedure described above for reductive amination. $^1$H-NMR (360 MHz, CDCl$_3$) δ 3.14-3.07 (m, 1H), 1.70-1.64 (m, 3H), 1.59-1.56 (m, 1H), 1.37-1.35 (m, 12H), 1.31-1.19 (m, 4H), 1.08-1.01 (m, 2H); $^{13}$C-NMR (90 MHz, CDCl$_3$) δ 53.10, 42.14, 41.71, 36.12, 36.09, 32.16, 32.03, 27.11, 24.39, 23.29, 21.93, 21.77, 16.39; ESI-MS: Calculated for C$_{13}$H$_{25}$N (M+H)$^+$ 196.3, Found: 196.3

Example 2

Plaque Reduction Assay Using Exemplary Compounds

FIG. 1 depicts the results of a plaque reduction assay of certain compounds according to the present disclosure on A/M2-V27A/L38F mutant influenza virus. The effects of the depicted compounds C$^1$, C$^2$, and C$^3$ on influenza A virus (A/Udorn/72) V27A/L38F mutant were evaluated by plaque formation on MDCK cells in the presence or absence of the compounds (10 μM or dose dependent). L38F is a natural mutation in Weybridge strain virus, which is pharmacologically silent to the drugs. Moreover, in Oocyte electrophyiosiocal recording, double mutant V27A/L38F M2 channel showed the indistinguishable channel activity and drug sensitivity as V27A single mutant M2 channel.

What is claimed:
1. A compound of formula (I):

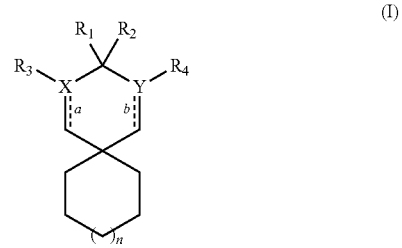

wherein
(a)
X and Y are independently a bond, alkylene, or amine;
$R^1$ is alkyl, hydroxyl, carbonyl, carboxyl, cyano, amino, —$CH(R^5)(R^6)$, or forms an oxo group together with $R^2$;
$R^2$ is alkyl, hydroxyl, carbonyl, carboxyl, cyano, amino, or —$CH(R^5)(R^6)$;
$R^3$ and $R^4$ are independently hydrogen or —$CH(R^7)(R^8)$;
$R^5$ and $R^6$ are independently hydrogen, alkyl, hydroxyl, carbonyl, or amino;
$R^7$ and $R^8$ are independently hydrogen, alkyl, alkoxy, hydroxyl, carbonyl, or amino;
dashed lines a and b are optional bonds; and,
n is 0-3, or,
(b)
X and Y are independently a bond, alkylene, or amine;
$R^1$ is hydrogen, alkyl, hydroxyl, carbonyl, carboxyl, cyano, —$CH(R^5)(R^6)$, or forms an oxo group together with $R^2$;
$R^2$ is hydrogen, alkyl, hydroxyl, carbonyl, carboxyl, cyano, or —$CH(R^5)(R^6)$;
$R^3$ and $R^4$ are independently hydrogen or —$CH(R^7)(R^8)$;
$R^5$ and $R^6$ are independently hydrogen, alkyl, hydroxyl, or carbonyl;
$R^7$ and $R^8$ are independently hydrogen, alkyl, alkoxy, hydroxyl, or carbonyl;
dashed lines a and b are optional bonds; and,
n is 0-3,
or,
(c)
X and Y are independently a bond, alkylene, or amine;
$R^1$ is amino, —$CH(R^5)(R^6)$, or forms an oxo group together with $R^2$;
$R^2$ is hydrogen, alkyl, hydroxyl, carbonyl, carboxyl, cyano, amino, or —$CH(R^5)(R^6)$;
$R^3$ is hydrogen or —$CH(R^7)(R^8)$;
$R^4$ is —$CH(R^7)(R^8)$;
$R^5$ and $R^6$ are independently hydrogen, alkyl, hydroxyl, carbonyl, or amino;
$R^7$ and $R^8$ are independently hydrogen, alkyl, alkoxy, hydroxyl, carbonyl, or amino;
dashed lines a and b are optional bonds; and,
n is 0-3,
or,
(d)
X and Y are independently a bond, alkylene, or amine;
$R^1$ is hydrogen, alkyl, hydroxyl, carbonyl, carboxyl, cyano, amino, —$CH(R^5)(R^6)$, or forms an oxo group together with $R^2$;
$R^2$ is hydrogen, alkyl, hydroxyl, carbonyl, carboxyl, cyano, amino, or —$CH(R^5)(R^6)$;
$R^3$ and $R^4$ are independently hydrogen or —$CH(R^7)(R^8)$;
$R^5$ and $R^6$ are independently hydrogen, alkyl, hydroxyl, carbonyl, or amino;
$R^7$ and $R^8$ are independently hydrogen, alkyl, alkoxy, hydroxyl, carbonyl, or amino;
at least one of lines a and b represents a bond; and,
n is 0-3,
or,
(e)
X is a bond or alkylene;
Y is methylene;
$R^1$ is amino, —$CH(R^5)(R^6)$, or forms an oxo group together with $R^2$;
$R^2$ is hydrogen, alkyl, hydroxyl, carbonyl, carboxyl, cyano, amino, or —$CH(R^5)(R^6)$;

$R^3$ is hydrogen or —$CH(R^7)(R^8)$;
$R^4$ is —$CH(R^7)(R^8)$;
$R^5$ and $R^6$ are independently hydrogen, alkyl, hydroxyl, carbonyl, or amino;
$R^7$ and $R^8$ are independently hydrogen, alkyl, alkoxy, hydroxyl, carbonyl, or amino;
dashed lines a and b are optional bonds; and,
n is 0-3,
or a stereoisomer, partial stereoisomer, prodrug, pharmaceutically acceptable salt, hydrate, solvate, acid hydrate, or N-oxide thereof.

2. The compound according to claim 1 wherein X and Y are each independently methylene or ethylene.

3. The compound according to claim 2 wherein X is methylene and Y is ethylene.

4. The compound according to claim 2 wherein at least one of $R^1$ and $R^2$ is hydrogen.

5. The compound according to claim 4 wherein one of $R^1$ and $R^2$ is carbonyl, amino, carboxyl, cyano, or —$CH(R^5)(R^6)$.

6. The compound according to claim 5 wherein n is 1 or 2, except that if n is 1, both X and Y are methylene, and both $R^3$ and $R^4$ are hydrogen, then one of $R^1$ and $R^2$ is not carbonyl.

7. The compound according to claim 5 wherein one of $R^1$ and $R^2$ is —$CH(R^5)(R^6)$.

8. The compound according to claim 7 wherein one of $R^5$ and $R^6$ is amino.

9. The compound according to claim 1 wherein said compound is:

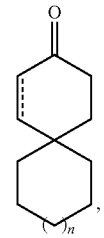

wherein n is 0, 2 or 3;

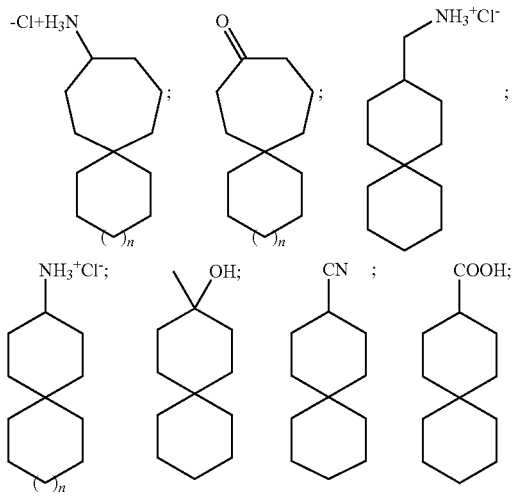

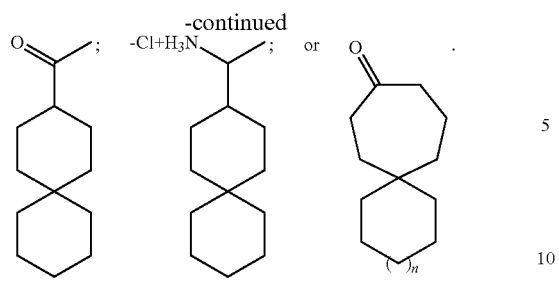
10. A composition comprising a compound according to claim 1 and a pharmaceutically acceptable carrier, diluent, or excipient.
* * * * *